United States Patent [19]

King et al.

[11] Patent Number: 4,868,343
[45] Date of Patent: Sep. 19, 1989

[54] ACID CATALYZED PROCESS

[75] Inventors: David L. King, Mountain View; Michael D. Cooper, San Jose; Michael A. Faber, Palo Alto, all of Calif.

[73] Assignee: Catalytica Inc., Mountain View, Calif.

[21] Appl. No.: 852,781

[22] Filed: Apr. 16, 1986

[51] Int. Cl.$^4$ ............................................. C07C 41/06
[52] U.S. Cl. ................................... 568/697; 526/135; 526/147; 526/172; 528/395; 536/115
[58] Field of Search ......................................... 568/697

[56] References Cited

U.S. PATENT DOCUMENTS

| | | | |
|---|---|---|---|
| 2,720,547 | 10/1955 | Wolff et al. | 568/697 |
| 4,148,695 | 4/1979 | Lee et al. | 568/697 |
| 4,376,219 | 3/1983 | Murofushi et al. | 568/697 |

*Primary Examiner*—Ronald W. Griffin
*Attorney, Agent, or Firm*—Robert J. Baran

[57] ABSTRACT

This invention provides an improved process for the conversion of reactant into a reaction product, in the presence of a solid acid catalyst comprising sulfonic acid groups covalently bonded to a polymeric chain, wherein the improvement comprises increasing the rate of conversion, on an equivalent sulfonic acid basis, by providing, as said polymeric chain a compound represented by the general formula:

$$M(O_3ZO_xR)_n$$

wherein M is a tetravalent metal ion; Z is a pentavalent atom, selected from the group consisting of elements of Group V of the Periodic Table of the Elements having an atomic weight greater than 30; x varies from 0 to 1; R is selected from the group consisting of organo radicals and mixtures of hydrogen radicals and organo radicals; and n varies from 1 to 2; provided that n is 1 when R is terminated with a tri-or tetraoxy pentavalent atom.

12 Claims, 2 Drawing Sheets

ACID CATALYZED PROCESS

FIELD OF THE INVENTION

This invention relates to an improved process for the acid-catalyzed conversion of a reactant into a reaction product. Reactants which may be converted into reaction products in the process of this invention include hydrocarbons and heteroatom-substituted hydrocarbons, wherein said heteroatoms may be selected from the group consisting of nitrogen, oxygen, sulfur, phosphorus and halogen atoms. For example, in the present inventive process, olefins may be isomerized, polymerized or oligomerized; olefins may be reacted with aromatics or tertiary alkanes to provide alkylated products; olefins may be reacted with carboxylic acids to obtain esters; olefins may be reacted with a peroxy acid to obtain an epoxide; alcohols may be dehydrated to obtain olefins or ethers or reacted with an aromatic compound or a carboxylic acid to obtain an alkylated product or an ester, respectively; anyhydrides may be reacted with an aromatic or an olefinic compound to obtain acetylated derivatives thereof; epoxides may be reacted to the corresponding glycols; aromatic compounds may be nitrated to provide nitro aromatics; etc.

BACKGROUND OF THE ART

Many chemical reactions are catalyzed by acidic catalysts. The acidic catalyst may be used in a homogeneous or heterogeneous mode, i.e. the catalyst can be dissolved in the reactant-containing solution or the catalyst may exist in a different phase than the reactant and/or the reaction products. Homogeneous acid catalysts may have certain advantages over heterogeneous acid catalysts, such as increased activity or selectivity, provided separation of the reaction products from the catalyst is easily carried out. Since such separation may be difficult, many times a heterogeneous acid catalyst is preferred, even when the activity or selectivity is less than a homongeneous catalyst in the same reaction. One widely used class of heterogeneous acid catalysts is the solid polystyrene sulfonic acids. These polymers are known to be effective as acid catalysts for many reactions, but, due to the organic polymer backbone, are not always as stable as desired. Moreover, the organic nature of the polymer may hinder polar reactants from contacting the functional sulfonic acid sites. In addition, the well known high temperatures utilized to remove such organic tars and crud from inorganic acid catalysts, such as zeolites, of course, cannot be used to reactivate polystyrene sulfonic acids because of the thermal instability of the organic polymer backbone.

SUMMARY OF THE INVENTION

The present invention provides a process for the conversion of a reactant into a reaction product in the presence of an acid catalyst which comprises contacting said reactant with an acid catalyst comprising a compound comprising sulfonic acid groups covalently bonded to a polymeric chain, wherein said polymeric chain is represented by the general formula:

wherein M is a tetravalent metal ion; Z is a pentavalent atom, selected from the group consisting of elements of Group V of the Periodic Table of the Elements having an atomic weight greater than 30; x varies from 0 to 1; R is selected from the group consisting of organo radicals and mixtures of hydrogen radicals and organo radicals; and n varies from 1 to 2; provided that n is 1 when R is terminated with a tri-or tetraoxy pentavalent atom. Preferably, M is selected from the group consisting of Zr, W, U, Ti, Th, Te, Sn, Si, Ru, Pu, V, Pr, Pb, Os, Nb, Mo, Mn, Ir, Hf, Ge, Ce and mixtures thereof and Z is P. More preferably Z is P and M is Zr.

Preferably, R is selected from the group consisting of alkyl, aryl and mixtures of alkyl and/or aryl and hydrogen or hydroxyl radicals.

More preferably R is selected from the group consisting of phenyl and mixtures of phenyl, hydrogen, hydroxyl and methyl radicals.

Preferably, n varies from 1.1 to 2.0, more preferably from 1.4 to 2.0. More preferably the polymeric chain is represented by the general formula:

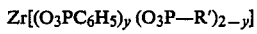

wherein y varies from 0.5 to 1 and R' is selected from the group consisting of hydrogen hydroxyl and methyl. Most preferably, R' is hydroxyl.

The present invention thus provides an improved process for the conversion of reactant into a reaction product, in the presence of a solid acid catalyst comprising sulfonic acid groups covalently bonded to a polymeric chain, wherein the improvement comprises increasing the rate of conversion, on an equivalent sulfonic acid basis, by providing, as said polymeric chain a compound represented by the above general formula.

The compounds, useful as acidic catalysts in the process of the present invention may be prepared, directly, according to the procedures described in U.S. Pat. Nos. 4,232,146; 4,235,990; 4,235,991; 4,256,872; 4,267,308; 4,276,409; 4,276,410; 4,276,411; 4,298,723; 4,299,943; 4,373,079; 4,384,981; 4,386,013; 4,390,690; 4,429,111; and 4,436,899 which are hereby incorporated by reference by reacting an organo sulfonic acid or organosulfonate substituted, pentavalent atom-containing acid or the polymeric chain may be formed, first, by the same procedures and subsequently sulfonated to provide the sulfonic acid groups. Preferably, the polymer chain is formed first and includes sulfonatable radicals, such as aromatic radicals and then said chain is reacted with a sulfonating agent such as oleum, to provide the acid catalyst for the process of this invention. In either case the polymer may be prepared having a layered structure similar to the layered structure of zirconium phosphate.

DESCRIPTION OF THE INVENTION

Figure 1:
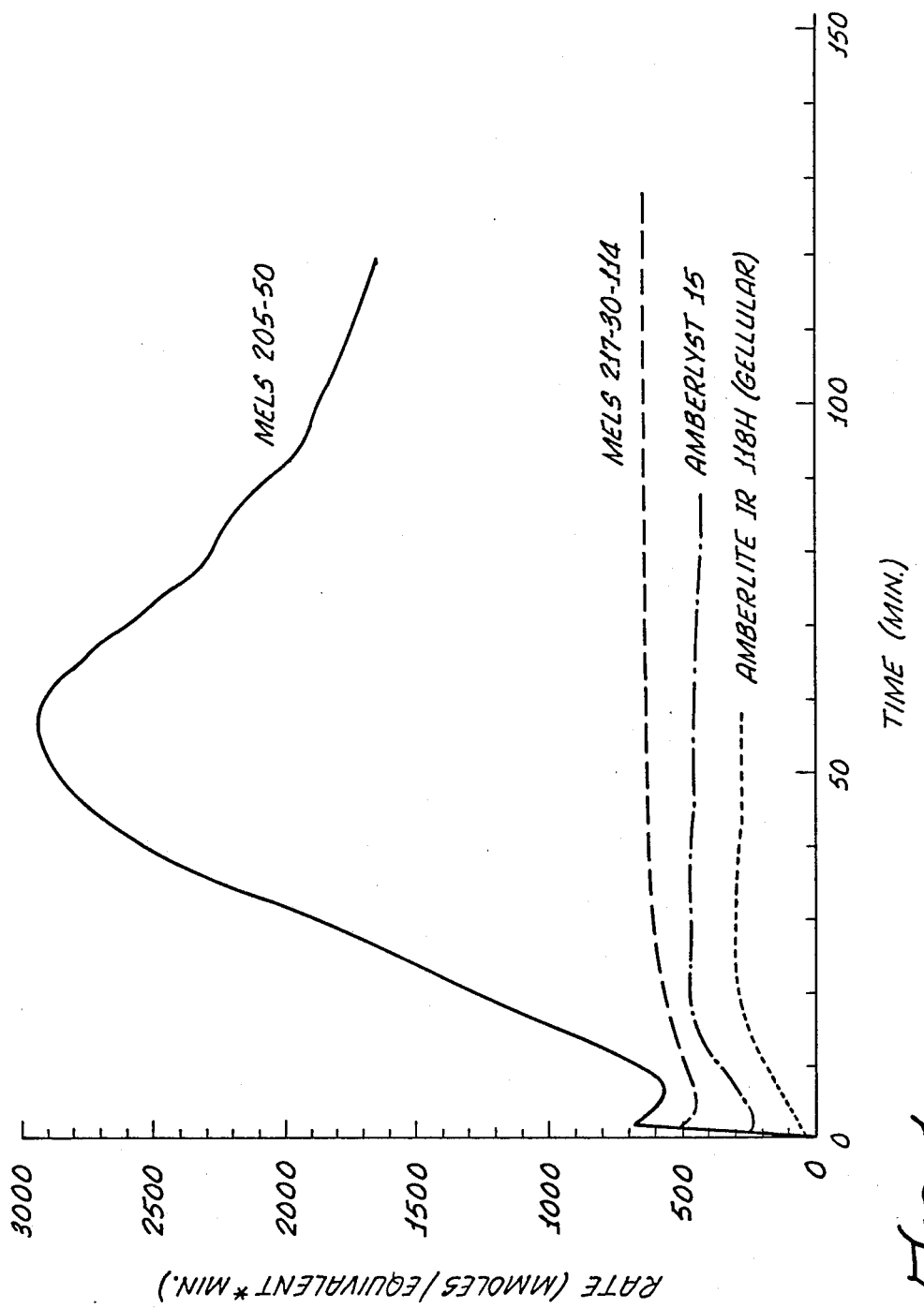
FIG. 1 shows the improved activity of two of the acid catalysts, utilized in the process of this invention, as compared to two polystyrene sulfonic acid resins on an equivalent sulfonic acid basis.

This invention provides an improved process for converting reactants, especially organic reactants, to reaction products in the presence of an acid catalyst. The improvement in said process is found in the choice of the compounds which function as the acid catalyst and are defined below. In particular, these compounds increase the rate of reaction, as compared to other well known acid catalysts, e.g. polystyrene sulfonic acids, (which comprises sulfonic acid groups pendant from a polystyrene polymer backbone) and are more stable with time and temperature, as compared to said polystyrene sulfonic acid catalysts.

Preferably, the reactants utilized in the process of this invention are hydrocarbons or hydrocarbons substituted with heteroatoms such as nitrogen, oxygen, sulfur, phosphorus and halogen atoms; and especially oxygen atoms.

Certain of the preferred reactants are unsaturated hydrocarbons such as olefins and aromatics. That is, olefins may be isomerized or oligomerized or polymerized in one embodiment of the process of this invention. For example, mono olefins having from four to ten carbon atoms may be isomerized or oligomerized or polymerized to reaction products in accordance with the present invention. A mixture of nonenes comprising predominantly 1-n-nonene is reacted to nonene dimer by heating at 130° C. for two hours in the presence of an acid catalyst comprising the compound utilized in Example 1, below. Propylene is heated for 1 hours, or more, at a temperature of from 50° to 175° C. and a pressure of from 1 to 50 atmospheres, in the presence of the compound of Example 1, to yield a mixture including as the predominant fraction monoolefins having from nine to twelve carbon atoms and useful as a polymer gasoline.

in another embodiment of this invention, the olefin is contacted with the acid catalyst, described below, in the presence of another reactant to yield reaction products of said olefin and said other reactant. Thus, said second reactant may include a hydroxyl group to yield an ether or an alcohol. For example, alkanols having from one to four carbon atoms may be reacted with olefins having from two to seven carbon atoms in the presence of the acid catalysts described below to yield ethers. Particularly preferred is the reaction of methanol and isobutylene, isoamylene or propylene to yield methyltertiary butyl ether, methyl-tertiary amyl ether or methyl isopropyl ether, respectively. Such reactions may take place at a temperature of from 15° to 200° C. and a pressure of from 1 to 10 atmospheres.

Olefins may also be contacted with a carboxylic acid in the process of this invention to yield esters. Thus, straight chain olefins, having from two to ten carbon atoms, isobutylene or cyclohexene may be reacted in the presence of carboxylic acids having from one to eight carbon atoms at a temperature within the range of 0° C. to 100° C. to yield the corresponding esters as the reaction product. U.S. Pat. No. 3,037,052 to Bortnick gives the details on this general reaction and is hereby incorporated by reference to show specific reactants and reaction conditions. Particularly preferred reactions, within this embodiment of the present process, include the reaction of monoolefins having from one to eight carbon atoms, more preferably from two to four carbon atoms, with methacrylic acid, acrylic acid, acetic acid or phthalic acid to obtain the corresponding esters. These esters of acrylic acid and methacrylic acid are useful monomers for the preparation of acrylic plastics and rubbers. The acetate esters, of course are useful as solvents. The phthalic esters are useful as plasticizers.

The olefin may also be reacted in the presence of an aromatic compound to provide alkylated aromatics. For example, propylene may be reacted with benzene to provided cumene. 1-n-olefins, having from six to twelve carbon atoms, may be reacted with phenol to provide alyklated phenols which may be subsequently reacted with ethylene oxide to provide nonionic surfactants such nonophenylethyleneoxide adducts. (Other alkylations of olefins, such as with tertiary alkanes, e.g. 1-n-butene and isobutane, to yield isoctane may also be carried out in the present process.)

Finally, the above olefins may be reacted in the presence of a peroxy acid compound to obtain an epoxide. In this manner, ethylene and propylene may be converted to ethylene oxide and propylene oxide, respectively. (Unsaturated oils and esters, such as soybean oil, oleic acid esters, tall oil esters may be epoxidized, similarly, in the presence of hydrogen peroxide.)

Other reactants useful in the process of the present invention include alcohols. Thus, in one embodiment of the invention alcohols, having from one to eight carbon atoms, more preferably from one to four carbon atoms, are reacted, in the presence of the acid catalyst described below, to yield either ethers or olefins (by dehydration). For example, methanol or ethanol may be reacted at a temperature of from 25° to 150° C. and a pressure of from 1 to 20 Atoms. to yield dimethyl ether or diethylether, respectively. Tertiary butanol may be dehydrated to isobutene at a temperature of from 50° to 175° C. Similarly, butanediol may be dehydrated to tetahydrofuran.

Like the olefin, alcohols may be reacted in the presence of a second reactant to provide reaction products of said alcohol and said second rectant. In particular, said second reactant may comprise a carboxylic acid group or an aromatic group to yield an ester or an alkylated aromatic, respectively. The reactants and the conditions for these reactions have been described above.

Another reactant that may be used in the process of the present invention is an anhydride. For example, anhydrides, such as acetic anhydride, may be reacted with a compound having an aromatic group or an olefinic group to yield acetylated aromatics or acetylated olefins, respectively. In particular, acetic anhydride may be reacted with anisole to provide p-methoxyacetophenone or with diisobutylene to provide 2,2-methyl, 6-oxo-hept-4-ene. These reactions can be carried out at a temperature of from 25° to 125° C. and a pressure of from 1 to 30 Atoms.

Aldehydes or ketones may be condensed to provide the respective condensed products by means of the process of the present invention. For example, 2-ethylhexenal may be prepared by condensing two molecules of n-butyraldehyde at a temperature of from 20° to 70° C. and a pressure of from 1 to 10 Atoms. Similarly, methylisobutylketone may be condensed to 1-methyl,4-methyl, 6-oxo, 9-methylnon-4-ene. In general, aldehydes and ketones, having from one to ten carbon atoms, may be condensed to provide dimers thereof in the process of the present invention.

In addition, the above aldehydes and ketones may be reacted in the presence of an aromatic compound to obtain the resulting reaction products. In particular, acetone may be reacted with phenol to yield bisphenol A and formaldehyde may be reacted with aniline to yield diaminodiphenylmethane.

Peroxides or hydroperoxides may be decomposed to the corresponding decomposition products by the process of this invention. For example, cumene hydroperoxide may be decomposed to acetone and phenol at low temperatures as compared to the non-acid catalyzed decomposition. Moreover, unlike the prior art polystyrene sulfonic acid catalysts, which are sensitive to heat (and thus the reactor must be designed to remove heat and avoid catalyst degradation), the acid catalysts of this invention are not heat sensitive.

Glycols may be prepared by utilizing an epoxide as the reactant in the process of the present invention. In particular, ethylene oxide and propylene oxide may be converted to ethylene glycol and propylene glycol, respectively.

Esters may be converted, efficiently, to carboxylic acid and alcohol in the present inventive process. For example, sucrose may be hydrolyzed to fructose and glucose.

The present process may also be utilized to provide nitroaromatics by utilizing as a reactant a mixture of an aromatic compound, e.g. benzene or toluene, and nitric acid. The reaction conditions for these reactions are well known in the art.

It is important to note that all of the above examples of reactants, reaction products and reaction conditions are known in the art. The present invention resides in the improvement to such process examples by use of the compounds described below, in detail, as the acidic catalyst to obtain increased rates of reaction, on an equivalent acid basis, as compared to other known catalysts, such as polystyrene sulfonic acid.

The acidic catalyst or the polymer backbone for said acid catalyst may be prepared by a process which comprises reacting, in a liquid medium, at least one acid compound, i.e. an organo-substituted, (or organo sulfonic acid-sub stituted) pentavalent atom containing acid, having the formula $$((HO)_2OZO_x)_kR(SO_3H)_z$$

wherein z is 1, when the sulfonic acid is prepared directly or 0 when the polymer is prepared for later sulfonation, k is 1 when n is 2 and k is 2 when n is 1, with at least one of the above tetravalent metal ions to precipitate a solid in which the molar ratio of pentavalent atom to tetravalent metal is 2 to 1, when x=0, the pentavalent atom is convalently bonded to R and when x equals 1, R is linked to the pentavalent element Z through oxygen.

It should be noted that x will be 0 when the starting material for preparing the compound is represented by the general formula $$((HO)_2Z_nR(SO_3H)_z$$
$$\|$$
$$O$$

wherein n is 1 or 2, e.g., $$((HO_2P)_nR(SO_3H)_z$$
$$\|$$
$$O$$

i.e., phosphorus acid or organophosphonic acids. When the starting material is represented by the general formula $$((HO)_2Z-O)_nR(SO_3H)_z;\ e.g.,\ ((HO_2P-O)_nR(SO_3H)_z,$$
$$\|\qquad\qquad\qquad\qquad\|$$
$$O\qquad\qquad\qquad\qquad O$$

i.e., organophosphoric acids or phosphoric acid, x will be 1. If a mixture of such starting materials are used, x will vary from 0 to 1 in accordance with the ratio of the starting materials.

Acid compounds useful for preparing the acidic catalyst directly include:

p-sulfophenyl phosphonic acid
m-sulfophenyl phosphonic acid
sulfoalkyl phosphonic acid, alkyl=methyl, ethyl, propyl, etc.

Preferably, the polymer backbone is formed, including a sulfonatable radical such as an aromatic or olefinic radical, and then sulfonated to obtain an acid catalyst for use in the improved process of the present invention. Thus, acid compounds useful for preparing a sulfonatable polymer backbone include:

phenylphosphonic acid
biphenyl diphosphonic acid
vinyl phosphonic acid
allyl phosphonic acid
isopropenyl phosphonic acid
1-propenylphosphonic acid.

Most preferably, the sulfonatable polymer backbone will comprise phenyl groups and mixtures of phenyl groups and mixtures of phenyl groups and hydrogen or hydroxyl groups. (Note under certain sulfonation conditions at least a portion of the hydrogen groups will be oxidized to hydroxyl groups to provide extremely active acidic catalyst.)

Sulfonic acid groups can be introduced onto the above polymer backbones by direct reaction with a sulfonating agent. Sulfonating agents such as oleum, sulfuric acid and chlorosulfonic acid can be used. Other sulfonating agents are acetyl sulfate i.e., the mixed anhydride of acetic acid and sulfuric acid ($CH_2COOSO_2H$). and sulfur trioxide complexes with dioxane, tetrahydrofuran, and trialkyl phosphates, or gaseous sulfur-trioxide The sulfonation reaction may be carried out from 25 seconds to 100 hours, preferably from 2 minutes to 2 hours, at temperatures from about —50° C. to 120° C., preferably from 0° C. to 80° C. The sulfonation procedures, useful in preparing acidic catalysts for use in the process of the present invention are disclosed in U.S. Pat. No. 3,642,728 and the references cited therein, which patent and references are hereby incorporated by reference.

The invention is further illustrated by the following examples which are illustrative of various aspects of the invention, and are not intended as limiting the scope of the invention as defined by the appended claims.

EXAMPLE 1

Dehydration of Alcohols

In this reaction, the reaction rate is monitored by measuring the flow of the olefin, i.e. isobutylene, which is a reaction product arising from the dehydration of tertiary-butanol according to the reaction:

$$t\text{-}C_4H_9OH \xrightarrow{H^+} i\text{-}C_4H_8 + H_2O$$

in the presence of the acidic catalyst described below. A small, continuous flow of isobutylene is maintained in the reactor to provide a positive pressure, as well as to initially saturate the t-butanol. (Due to the high solubility of isobutylene in t-butanol, pressurization is required; otherwise, the reaction products, i.e. isobutylene, would dissolve in the reactant, i.e. isobutanol, and would not be observed. The reaction rate is monitored continuously and is the difference between the outlet isobutylene flow and the inlet isobutylene flow.)

To a 2000 ml flask, 2.0 grams of the catalyst described below is then added to initiate the dehydration reaction and the resulting two-phase mixture is agitated.

The isobutylene evolved from the t-butanol is measured as a function of time and is taken as an indication of reaction progress; with time=0 taken as the point at which the catalyst is added to the tertiary-butanol. An induction period is observed, after which the reaction rate increases to a maximum and, over a long period of time, the catalyst activity declines as the teritary butanol becomes rich in reaction product water. The water accumulates at the acid site, thereby "levelling" the acidity.

Figure 2:
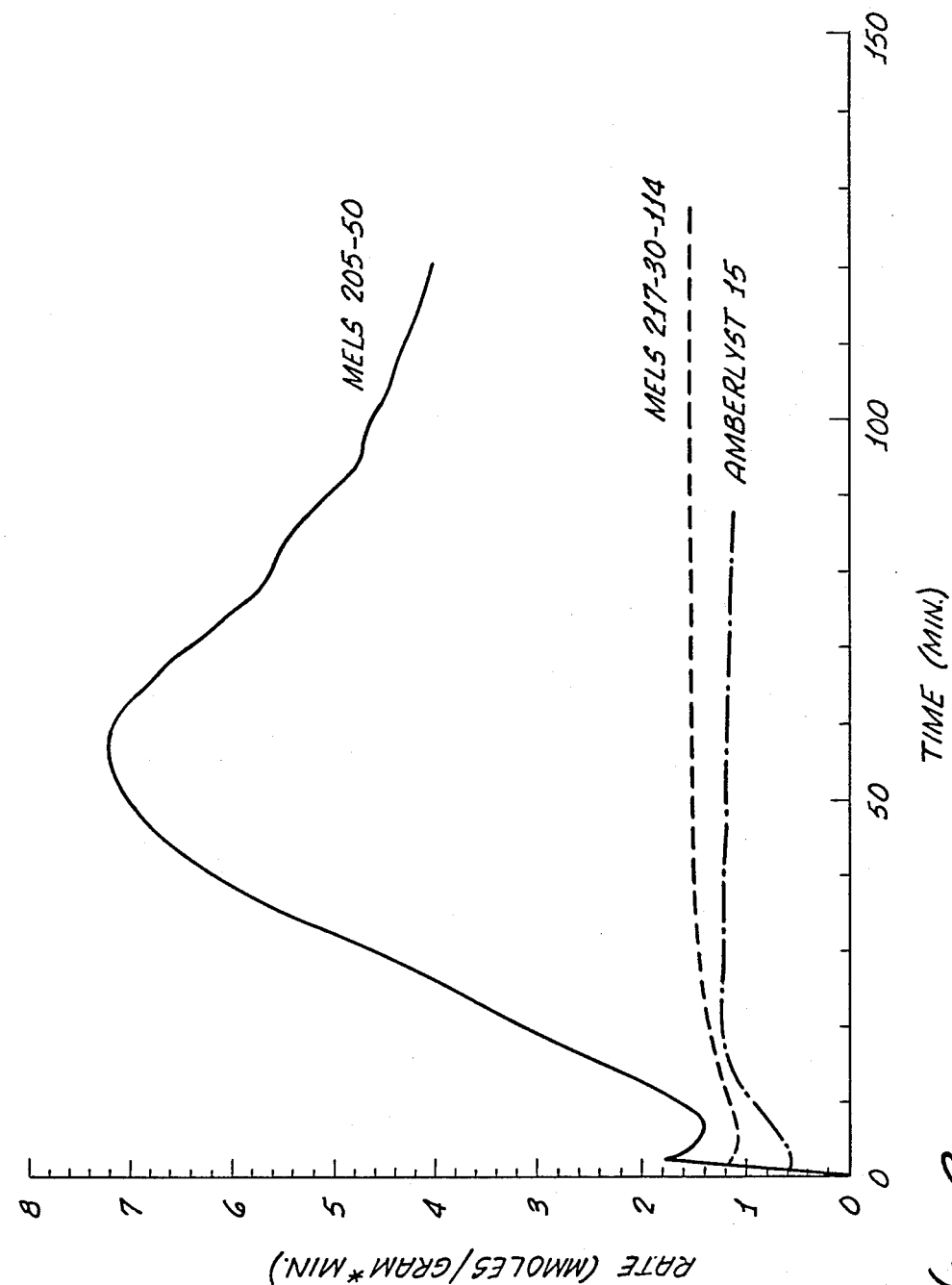
FIG. 2 shows the same improvement on an equivalent weight basis.

The results of experiments comparing two of the catalysts, utilized in the improved process of this invention, as compared to two representative polystyrene sulfonic acid catalysts of the prior art, are given in FIGS. 1 and 2. The acid catalysts, utilized in the process for the dehydration of tertiary-butanol, may be identified as follows:

Amberlite IR-118H Strong Acid (Sulfonated polystyrene) ion exchange resin, gellular form; 1.76 milliequivalents $SO_3H$ per gram Amberlyst 15 Strong acid (Sulfonated polystyrene) ion exchange resin, macroreticular form; 2.5 milliequivalents - $SO_3H$ per gram (wet)

MELS 217-2-97 $Zr(O_3PC_6H_5SO_3H)_1(O_3PCH_3)_1$ 1.21 milliequivalents - $SO_3H$ per gram MELS 205-50 $Zr(O_3PC_6H_5SO_3H)_{2/2}(O_3PH)_{2/2}$ 2.94 milliequivalents - $SO_3H$ per gram.

Both acid catalysts designated MELS were prepared by treating a high surface area phenyl/$CH_3$ or phenyl/H precursor compound with oleum ($H_2SO_4/SO_3$, fuming sulfuric acid) at 60° C. for 20 minutes, followed by dilution with water and sequential washes with water and/or diethylether to remove residual $H_2SO_4$. The acid catalyst was dried, characterized, and ground to a fine powder for addition to the reactor containing isobutylenesaturated t-butanol.

Each of the MELS catalysts were characterized by thermogravimetric analysis, infrared spectroscopy, surface area and were titrated to obtain acidity per site data. The equivalent point of the titration was taken at PH=6. The infrared spectra confirmed the presence of sulfonation through clear evidence of transition from monosubstituted to disubstituted aromatic. It can be seen from the figures that the activity per site is unexpectedly higher for the MELS catalysts. The greater activity of the catalysts utilized in the process of this invention enables one to obtain greater product throughput per catalyst volume or use less catalyst to achieve equal productivity. In addition, this greater activity enables one to operate any of the acid catalyzed processes, disclosed herein, at lower temperatures thereby extending catalyst life and minimizing the formation of higher temperature by products. At maximum turnover, the activity persite of the MELS 205-50 catalyst is approximately twelve times the activity of the polystyrene sulfonic acid catalysts of the prior art. The catalyst designated MELS 205-50 is determined to include hydroxyl moieties thus indicating that the phosphite moiety has been oxidized to a phosphoric acid moiety, thus further increasing the activity of the acidic catalyst. This catalyst is utilized in the following experiments.

EXAMPLE 2

To a 300 ml. stainless steel rocking autoclave are charged toluene (92 g., 1 mole), propylene (41 g., 0.975 mole) and 13 g. of the catalyst of Example 1. The bomb is heated over 30 minutes to 100° C. (109° C. jacket temperature) and the heat shut off. At this point, there is a pressure of 300 psig. The temperature rises to 120° C. and the pressure falls to 100 psig, over the next ten minutes. The bomb is shaken for 2 hours more, then chilled and opened. The liquid is distilled to give a cut that is mainly o-isopropyltoluene with lesser amounts of meta and para isomers. Another cut is mostly 2,4-diisopropyltoluene and the bottom is mostly 2,4,6-triisopropyltoluene.

EXAMPLE 3

In this example, the reaction between isobutylene and acetic acid to give tertiary-butyl acetate is catalyzed by the acid catalyst of Example 1. This is accomplished either batchwise or in a continuous flow reactor. At a 2.4 to 3.3 mole ratio of acetic acid to isobutylene, 85 percent conversion to t-butyl acetate, based on isobutylene, is achieved utilizing a fixed bed reactor and 9-10 minutes contact time. Polymerization is not significant as only from a trace to 1.6 percent of $C_8H_{16}$ is detected. The reaction conditions for this reaction is described in U.S. Pat. No. 3,678,099 to Kemp, which is hereby incorporated by reference.

While particular embodiments of the invention have been described it will be understood of course that the invention is not limited thereto since many obvious modifications can be made and it is intended to include within this invention any such modifications as will fall within the scope fo the appended claims.

What is claimed is:

1. In a process for the conversion of an olefin and an alkanol into an ether in the presence of a solid acid catalyst comprising sulfonic acid groups covalently bonded to a polymeric chain, the improvement comprising increasing the rate of conversion, on an equivalent sulfonic acid basis, by providing, as said polymeric chain a compound represented by the general formula:

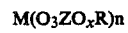

$$M(O_3ZO_xR)_n$$

wherein M is a tetravalent metal ion; Z is a pentavalent atom, selected from the group consisting of elements of Group V of the Periodic Table of the Elements having an atomic weight greater than 30; x varies from 0 to 1; R is selected from the group consisting of organo radicals and mixtures of hydrogen radicals and organo radicals; and n varies from 1 to 2; provided that n is 1 when R is terminated with a tri-or tetraoxy pentavalent atom.

2. The process of claim 1 wherein said olefin comprises from two to seven carbon atoms and said alkanol comprises from one to four carbon atoms.

3. The process of claim 2 wherein said alkanol is methanol and said oelfin is selected from the group consisting of isobuylene, isoamylene and propylene.

4. The process of claim 1 wherein M is selected from the group consisting of Zr, W, U, Ti, Th, Te, Sn, Si, Ru, Pu, V, Pr, Pb, Os, Nb, Mo, Mn, Ir, Hf, Ge, Ce and mixtures thereof.

5. The process of claim 4 wherein Z is P and M is Zr.

6. The process of claim 5 wherein R is selected from the group consisting of alkyl, aryl and mixtures of alkyl and/or aryl and hydrogen radicals.

7. The process of claim 6 wherein R is selected from the group consisting of phenyl and mixtures of phenyl, hydrogen and methyl radicals.

8. The proecss of claim 7 wherein said compound is represented by the general formula:

$$Zr[(O_3PC_6H_5)_y (O_3P-R')_{2-y}]$$

wherein y varies from 0.5 to 1 and R' is selected from the group consisting of hydrogen and methyl.

9. The process of claim 1 wherein said conversion is effected at a temperature of from 15° C. to 200° C. and a pressure of from 1 Atms. to 10 Atms.

10. The process of claim 1 wherein said reactant is contacted with said solid acid catalyst in the liquid phase.

11. The process of claim 1 wherein said solid acid catalyst is prepared by forming, as said polymeric chain, a polymeric chain comprising aromatic radicals and sulfonating said aromatic radicals with a sulfonating agent.

12. The process of claim 11 wherein said sulfonating agent is oleum.

* * * * *